United States Patent
Bonrath et al.

(10) Patent No.: US 8,563,780 B2
(45) Date of Patent: Oct. 22, 2013

(54) ALLYL AND PROPARGYL ETHERS

(75) Inventors: Werner Bonrath, Freiburg (DE); Rolf Kuenzi, Basel (CH)

(73) Assignee: DSM IP Assets B.V., Heerlen (NL)

( * ) Notice: Subject to any disclaimer, the term of this patent is extended or adjusted under 35 U.S.C. 154(b) by 11 days.

(21) Appl. No.: 12/990,709

(22) PCT Filed: May 12, 2009

(86) PCT No.: PCT/EP2009/055692
§ 371 (c)(1),
(2), (4) Date: Aug. 19, 2011

(87) PCT Pub. No.: WO2009/138389
PCT Pub. Date: Nov. 19, 2009

(65) Prior Publication Data
US 2012/0029240 A1  Feb. 2, 2012

(30) Foreign Application Priority Data

May 13, 2008 (EP) .................................. 08008829
Jul. 7, 2008 (EP) .................................. 08012216
Oct. 9, 2008 (EP) .................................. 08166175

(51) Int. Cl.
*C07C 45/00* (2006.01)
*C07C 43/303* (2006.01)
*C07C 41/54* (2006.01)

(52) U.S. Cl.
USPC ............ 568/386; 568/405; 568/591; 568/596

(58) Field of Classification Search
USPC .................. 568/386, 405, 591, 596
See application file for complete search history.

(56) References Cited

PUBLICATIONS

International Search Report for PCT/EP2009/055692, mailed Oct. 20, 2009.
Written Opinion of the International Searching Authority for PCT/EP2009/055692, mailed Oct. 20, 2009.
Saucy, G. et al., "Uber Die Reaktion Von Tertiaren Vinylcarbinolen Mit Isopropenylather, Eine Eue Methode Zur Herstellung Von Gamma, Delta-Ungesattigten Ketonen", Helvetica Chimica. Acta, Verlag Helvetica Chimica Acta., vol. 50, No. 218, (Jan. 1, 1967), pp. 2091-2095.
Saucy, G. et al., "Uber Eine Neuartige Synthese Von Beta-Ketoallenen Durch Reaktion Von Tertiaren Acetylencarbionolen Mit Vinylathern. Eine Ergiebige Methode zur Darstellung Des Pseudojonons Und Verwandter Verbindungen", Helvetica Chimica Acta, vol. 50, No. 4, (Jan. 1, 1967), pp. 1158-1167.
Frauchiger, S. et al., "Saucy-Marbet Ketonization in a Continuous Fixed-Bed Catalytic Reactor", Applied Catalysis A: General, vol. 253, No. 1, (Oct. 20, 2003), pp. 33-48.
Tutorskaya, O.O. et al., "Synthesis of 4-Hydroxy-2,5-Cyclohexadien-1-Ones With Isoprenoid Substituents of Varying Structure", Database CA [Online], Database Accession No. 1992:173610, (1991), Abstract.
Miropol'Skaya, M.A. et al., "Synthetic Studies of Polyene Compounds. XXXVIII. Role of an Acid Catalyst in the Reaction of Dihydrolinalool with Methylisopropenyl Ether", Database CA [Online], Database Accession No. 1974:568843, (1974), Abstract.
Zakharova, P.I. et al., "Synthetic Studies in a Series of Polyene Compounds. XXXIII. Preparation and Rearrangements of Acetone(3-Methyl-1-Penten-4-Yn-3-Yi )Methyl Acetal", Database Ca [Online], Database Accession No. 1971:509784, (1971), Abstract.

*Primary Examiner* — Sikarl Witherspoon
(74) *Attorney, Agent, or Firm* — Nixon & Vanderhye P.C.

(57) ABSTRACT

Allyl and propargyl ethers of the formula $X-C(R^1)(R^2)-O-C(CH_3)(R^3)-OCH_3$ (I), wherein X is an ethynyl or vinyl group, $R^1$ is methyl or ethyl, $R^2$ is a saturated or unsaturated linear or cyclic aliphatic hydrocarbon residue and $R^3$ is methyl or ethyl, a method for their preparation and their use in the manufacture of β-ketoallenes, α,β-unsaturated carbonyl compounds and γ,δ-unsaturated ketones.

21 Claims, No Drawings

ALLYL AND PROPARGYL ETHERS

This application is the U.S. national phase of International Application No. PCT/EP2009/055692 filed 12 May 2009, which designated the U.S. and claims priority to EP Application No. 08008829.7 filed 13 May 2008; EP Application No. 08012216.1 filed 7 Jul. 2008; and EP Application No. 08166175.3 filed 9 Oct. 2008, the entire contents of each of which are hereby incorporated by reference.

The present invention relates to allyl and propargyl ethers, to processes for their preparation and to their uses.

More precisely the invention relates to allyl and propargyl ethers of the general formula X—C($R^1$)($R^2$)—O—C(CH$_3$)($R^3$)—OCH$_3$ (I), wherein X is an ethynyl or vinyl group; $R^1$ is methyl or ethyl, $R^2$ is a saturated or unsaturated linear or cyclic aliphatic hydrocarbon residue and $R^3$ is methyl or ethyl, and to a process of their preparation by reacting a tertiary ethynyl or vinyl carbinol of formula X—C($R^1$)($R^2$)—OH (II) with isopropenyl methyl ether (IPM) or 2-n-butenyl methyl ether (BME) in the presence of an acid catalyst. The compounds of formula (I) are, therefore, also addressed as IPM- and BME-adducts, respectively.

Saucy et al. (Helv. Chim. Acta 50 (1967), 1158) have described the preparation of β-ketoallenes in high yields by reacting acetylene carbinols with vinyl ethers in inert solvents at temperatures of 60-80° C. and in the presence of catalytic amounts of p-toluenesulphonic acid or phosphoric acid. They had reasons to propose that the reaction proceeds via a propargyl intermediate of formula (I) wherein X is ethynyl but were unable to isolate and identify this intermediate.

Similarly, Saucy et al. (Helv. Chim. Acta 50 (1967), 2091) have described the preparation of γ,δ-unsaturated ketones in high yields (73-94% relative to the carbinol) by reacting tertiary vinyl carbinols with isopropenyl ethers under pressure, at temperatures of 120-200° C. during 12-16 hours, in the presence of catalytic amounts of phosphoric acid. Working without pressure resulted in far less yields, e.g., only 41% instead of 93% in case of 6-methyl-5-hepten-2-one (MH). Again, the authors postulate that the reaction precedes via intermediates of formula I wherein X is vinyl and admit that they have been unable to isolate and identify these compounds.

It has now been found in accordance with the present invention that by carrying out the reaction of MBE with IPM at a temperature of −20° C. or below the postulated intermediates of formula (I) which have so far not been described in the literature can be isolated in high yields and purity before being transferred into valuable known compounds.

The present invention, therefore, relates to allyl and propargyl ethers of the general formula X—C($R^1$)($R^2$)—O—C(CH$_3$)($R^3$)—OCH$_3$ (I), wherein X is an ethynyl or vinyl group; $R^1$ is methyl or ethyl, $R^2$ is a saturated or unsaturated linear or cyclic aliphatic hydrocarbon residue and to a process for their preparation by reacting a tertiary ethynyl or vinyl carbinol of formula X—C($R^1$)($R^2$)—OH (II) with isopropenyl methyl ether (IPM) or 2-n-butenyl methyl ether (BME) at a temperature of −20° C. or below, in the presence of an acid as catalyst. The invention also relates to the use of the new compounds for the manufacture of known β-ketoallenes, α,β-unsaturated carbonyl compounds and γ,δ-unsaturated ketones, e.g., MH (6-methyl-5-heptene-2-one) and a corresponding method for the manufacture of the latter.

Saturated or unsaturated linear or cyclic aliphatic hydrocarbon residues comprise straight-chain or branched-chained alkyl, alkenyl and alkynyl groups with one or more double or triple bonds as well as cycloalkyl and cycloalkenyl groups, having 1 to 46 carbon atoms. Preferred examples of such groups $R^2$ are methyl, CH$_2$-prenyl, CH$_2$-geranyl, CH$_2$-farnesyl, CH$_2$-hexahydrofarnesyl, CH$_2$-solanesyl and CH=CH-(2,6,6-trimethylcyclohex-1-enyl).

The starting compounds, viz. the tertiary ethynyl and vinyl carbinols as well as IPM and BME, are well-known in the art. They are commercially available or can be produced by methods well-known in the art.

While any strong organic or inorganic acid can be used as catalyst in the process of the present invention it is advantageous to use an acid which allows working in homogeneous phase. Preferred acids are selected from those with a pKa in the range of from 1.5 to 4.5. Among the acids which come into consideration phosphoric acid has turned out to be the preferred acid, in an amount of 0.5-2.0 mol-%, preferably 1.0 mol-%.

Experiments carried out at temperatures below 0° C. resulted in a higher yield and higher product quality but required longer reaction times and higher amounts of phosphoric acid. A suitable temperature for the reaction is a temperature below −20° C. and a suitable temperature range is about −30° C. to −20° C.

It is advantageous to use an excess of IPM or BME relative to compound (I). The excess can be up to 20 mol equivalents, preferably 5.0-12.5 mol equivalents, more preferably 5.0-7.5 mol equivalents.

The reaction can be carried out in the absence or presence of an inert solvent, preferably without solvent or in a hydrocarbon, e.g., pentane, hexane or heptane.

After termination of the reaction, i.e., normally after 24-72 hours, the reaction mixture is neutralized with a weak base, e.g., an amine or salts of weak acids and strong bases such as sodium acetate. A preferred base in the present situation is triethylamine.

By the use of normal isolation techniques the compounds of formula (I) can be isolated in a purity of at least 80%, preferably at least 90% and most preferably at least 95% in yields of at least 80%, preferably up to 85% and even more (up to 90% relative to compound (II)). The products thus obtained are stable at −20° C. for several months while they decompose when stored for more than 60 days at room temperature (22° C.). A preferred compound of formula (I) is 3-(1-methoxy-1-methylethoxy)-3-methyl-1-butene (MMMB) which is an intermediate in a process for the preparation of 6-methyl-5-heptene-2-one (MH) from 2-methyl-3-buten-2-ol (MBE) and IPM. Other preferred compounds of formula (I) are, e.g., 3-(1-methoxy-1-methylethoxy)-3-methyl-5-(2,6,6-trimethyl-cyclohex-1-enyl)-1-pentyne-4-ene and 3-(1-methoxy-1-methylethoxy)-3-methyl-5-(2,6,6-trimethyl-cyclohex-1-enyl)-1,4-pentadiene from which, e.g., vitamin A or flavor intermediates can be prepared.

The products can either be directly transferred into the desired β-ketoallene or γ,δ-unsaturated ketone without being isolated from the reaction mixture or first being further purified in accordance with methods well-known in the art, e.g. by adsorption/desorption on suitable solid basic carriers, such as aluminum oxide, silica and weak basic ion exchangers. A particularly suitable agent for further purification is aluminum oxide basic, commercially available, e.g., Alox B, class A-I. It is essential to add some water to the dry aluminum oxide, viz. in the range of 3-7 weight-%, preferably about 5 weight-% for partial deactivation. It is also favourable to work under a protective gas, such as argon, and to use a hydrocarbon as solvent, e.g. pentane or hexane.

The compounds of formula (I) can be transferred into the desired β-ketoallenes (when X=ethynyl) or γ,δ-unsaturated ketones (when X=vinyl), respectively, by heating them to 100-160° C., preferably 120-150° C., optionally in the presence of a solvent, in the presence or absence of a catalyst. Preferred catalysts are acids, especially mineral acids, e.g., sulfuric acid and phosphoric acid. The reaction, which can be carried out batch-wise or continuously, can be effected without or, preferably, with additional IPM. An excess of 0.1-5.0 equivalents, preferably 0.5-3.5 equivalents and most preferably 1.0-3.0 equivalents (mol/mol) of IPM is appropriate.

The BME-adducts of formula I can be transferred in a similar manner into n- and iso-unsaturated compounds, e.g., BME-dihydrolinalool-adducts into n- and iso-isonaline (which are β-ketoallenes) and further into n- and iso-methylpseudoionone and n- and iso-α-isonaline (which are all α,β-unsaturated ketones), respectively, by methods well-known in the art.

The present invention, therefore, also comprises a method for the manufacture of β-ketoallenes or γ,δ-unsaturated ketones, which method is characterized in that a compound of formula I is heated to 100-160° C., preferably 120-150° C., optionally in the presence or absence of a catalyst, preferably in the presence of an acid, and optionally with additional IPM. In a preferred embodiment the compounds of formula I are the addition products (adducts) of linalool, dehydrolinalool, nerolidol, 2-solanesyl-1-methyl-1-ethinyl-ethanol, vinyl-β-ionol or ethinyl-β-ionol with IPM or BME.

It has further been found and is, therefore, also part of the present invention that a compound of formula I can be reacted with 2,2-dimethoxypropane (DMP, III) in the presence of an acid to form a γ,δ-unsaturated ketone of formula $(R^1)(R^2)C=Y-CH_2-CO-R^3$ (IV) wherein $R^1$, $R^2$ and $R^3$ are as defined above and Y is C=CH or CH—CH$_2$. In a preferred embodiment of this reaction the compound of formula I is 3-(1-methoxy-1-methylethoxy)-3-methyl-1-butene (the MBE-IPM-adduct or MMMB) and the γ,δ-unsaturated ketone of formula III is MH (6-methyl-5-heptene-2-one).

With respect to the acid which can be used in this reaction the same applies what has been said above for the formation of compounds of formula I. The preferred acid is phosphoric acid. The reactants I and III are reacted in a molar ratio of 1:1-10, preferably 1:1,5-5, more preferably 1:2-4. The temperature is conveniently in the range of 100-170° C., preferably in the range of 130-160° C. and the reaction is nearly complete after 24 hours with yields of about 80%.

Finally, it has been found surprisingly in connection with the present invention and, therefore, also forms part of the present invention that in a phosphoric acid catalyzed reaction MBE and DMP form MH. The reaction conditions are the same as for the reaction of compounds I and III. The reaction is nearly complete after 24 hours with yields of about 52%.

The invention is illustrated in more detail by the following examples:

EXAMPLE 1

Phosphoric Acid Catalyzed IPM-Addition to MBE

Reaction

A mixture of 52.2 g (0.592 mol) of 2-methyl-3-buten-2-ol (MBE) and of 331.9 g (4.44 mol) of isopropenyl methyl ether (IPM) was stirred by a magnetic stirrer in a 1 L 3-neck round bottomed flask under argon at a temperature of −30° C. 3.72 g of a catalyst solution consisting of 17.7 weight-% H$_3$PO$_4$ in acetone (=1 mol-% relative to MBE) were added at once with the help of a volume adjustable pipette with disposable tip. The clear and colourless solution was stored for 72 hours at a temperature of −26° C. in a deep freezer. Under stirring and argon the solution was set basic by addition of 1.81 g (2.485 ml, 0.018 mol) of triethylamine and allowed to reach room temperature (22° C.). The reaction mixture was then concentrated on a rota-vapor under a pressure of 75 mbar at a temperature not exceeding 22-25° C. 94.9 g of crude 3-(1-methoxy-1-methyl-ethoxy)-3-methyl-but-1-ene, including 2.4 g of triethylammonium phosphate, were obtained containing 88.4 g of MMMB or MBE-IPM-adduct (yield: 87.2% relative to MBE).

Purification 12.2 g of deionized water were added to 232 g of dry Alox B, class A-I, in a 4-necked reaction flask and the mixture was mixed with a glass rod by hand until a homogeneous powder was obtained. A PT-100 thermo-couple was set into the reaction flask. The hot powder was cooled down under argon in an ice-bath until room temperature (22° C.) was reached. 94.4 g of the crude MMMB were transferred with 116 g of pentane to the Alox B, containing now 5 weight-% of water. A KPG glass propeller stirrer was set in the reaction flask and the paste was stirred (400-500 rpm) at room temperature (22° C.) for 2 hours. The product in pentane was separated from Alox B by filtration over a 5 µm Teflon filter. The filter cake was washed with about 2000 ml of pentane. The extract was concentrated on a rota-vapor under a pressure of max. 25 mbar and a temperature of max. 25° C. 78.9 g of MMMB were obtained as a colourless oil with a purity of 96.5% in 81 weight-% yield (relative to MBE). Structure and quality were confirmed by GC and NMR spectroscopy.

NMR Parameter

NMR spectra were recorded on a Bruker Avance 300 spectrometer equipped with 5 mm BBO BB-1H probe head operating at 300 MHz for $^1$H and 75.5 MHz for $^{13}$C. Spectra were recorded in CDCl$_3$ and referenced to TMS ($δ_H$) or solvent signals (δc): $δ_H$ 0.00/δc 77.0. Assignments were based on $^1$H and $^{13}$C-NMR spectral data taking into account coupling constants and chemical shifts; multiplicity for $^{13}$C is given as implied by DEPT: C=s, CH=d, CH$_2$=t, CH$_3$=q.

Formula

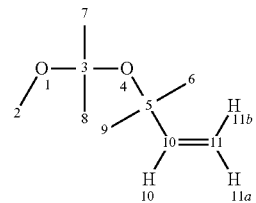

Molecular formula $C_9H_{18}O_2$
Monoisotopic mass 158.1307
Chemical name (CAS) 3-(1-methoxy-1-methyl-ethoxy)-3-methyl-but-1-ene $^1$H-NMR δ 6.12 (1H, dd, J=17.6, 10.8 Hz, H-10a), 5.08 (1H, dd, J=17.6, 1.1 Hz, H-11b), 4.97 (1H, dd, J=10.8, 1.1 Hz, H-11a), 3.25 (3H, s, H$_3$-2), 1.37 (4×3H, 4×s, H$_3$-6, H$_3$-7, H$_3$-8, H$_3$-9).

$^{13}$C-NMR δ 146.9 (d, C-10), 110.9 (t, C-11), 101.3 (s, C-3), 75.5 (s, C-5), 48.2 (q, C-2), 28.6 (2×q, C-6 & C-9, 27.3 (2×q, C-7 & C-8).

EXAMPLE 2

Phosphoric Acid Catalyzed BME-Addition to Dehydrolinalool (DLL)

Reaction

A mixture of 19 g DLL (0.1236 Mol) and 81.4 g of BME (0.927 Mol) was stirred (magnetic stirrer) in a 250 ml-neck round bottomed flask under argon at a $T_I$=−20° C. ($T_J$=ca. −25° C.). 0.341 g of a catalyst solution (H$_3$PO$_4$ 17.7 w % in acetone, 0.618 mMol=0.5 Mol % relative to DLL) were added at once with the help of a volume adjustable pipette with disposable tip. This clear and colorless solution was stored for 24 hours at $T_f=-20°$ C. in a deep freezer of ca. $-22°$ C. Out of the deep-freezer, still at $T_f=-20°$ C., under stirring and argon, the solution was set basic with 260 µl of triethylamine and stirred until room temperature was reached. The reaction mixture was then concentrated on a rota-vapor with a membrane-pump (10 mbar) and degassed with a high-vacuum pump (0.02 mbar on pump). During this process and the following work-up the temperature of the DLL-BME-adduct should not exceed 22-25° C. 28.1 g of crude product were isolated, containing 85.9 area % DLL-BME-adduct, yield 81.9%.

Enrichment 8.86 g of deionized water were added to 168 g of Alox B, class I (dry) in a 4-neck reaction flask and then mixed by hand with a glass rod till a homogenous powder was obtained. A PT-100 thermo-couple was set into the reaction flask. The hot powder was cooled down under argon in an ice-bath until room temperature was reached. 28.1 g of the crude product were transferred with 84 g of pentane to the Alox B, containing now 5 w % of water. A KPG glass propeller stirrer was set in the reaction flask. The paste was stirred (400-500 rpm) at room temperature for 2 hours. The product in pentane was separated from the Alox B by filtration over a 5 µm Teflon filter. The filter cake was washed with ~1000 ml of pentane. The extract was concentrated on a rota-vapor with a membrane-pump (10 mbar) and degassed with a high-vacuum pump (0.02 mbar on pump) at a max. temperature of $T_f=25°$ C. 22.3 g enriched DLL-BME-adduct were obtained, purity 97.8 area %, yield 74.1; recovery of the DLL-BME-adduct over the enrichment process 90.5%. The remaining Alox B was once again washed with ~500 ml of pentane. The extract was concentrated on a rota-vapor with a membrane-pump (10 mbar) and degassed with a high-vacuum pump (0.02 mbar on pump) at a max. temperature of $T_f=25°$ C. 1.2 g of a second enriched DLL-BME-adduct were obtained, purity 94.1 area %, yield 3.8%; recovery of the DLL-BME-adduct over the enrichment process 4.7%.

Two diastereomeric DLL adducts, (3R*)-3-{[(1R*)-1-methoxy-1-methylpropyl]oxy}-7-methyloct-6-en-1-yn-3-ol and (3R*)-3-{[(1S*)-1-methoxy-1-methylpropyl]oxy}-7-methyloct-6-en-1-yn-3-ol were characterised as a mixture. Assignment of the NMR datasets to the diastereomers was not investigated.

DLL-BME-Adduct 1:
$^1$H-NMR: δ=5.14 (1H, m, H-6), 3.19 (3H, OCH$_3$), 2.43 (1H, s, H-1), 2.19 (2H, m, H$_2$-5), 1.76 (4H, m, H$_2$-4, H$_2$-2'), 1.69 (3H, s, H$_3$-8), 1.63 (3H, s, CH$_3$-7), 1.57 (3H, s, H$_3$-1'), 1.54 (3H, s, CH$_3$-3), 0.88 (3H, t, J=7.5 Hz, H$_3$-3').
$^{13}$C-NMR: δ=131.7, 124.1, 104.2, 87.9, 72.4, 70.1, 48.0, 45.2, 31.4, 27.9, 25.7, 23.1, 22.9, 17.6, 8.6.

DLL-BME-Adduct 2:
$^1$H-NMR: δ=5.14 (1H, m, H-6), 3.23 (3H, OCH$_3$), 2.45 (1H, s, H-1), 2.19 (2H, m, H$_2$-5), 1.76 (4H, m, H$_2$-4, H$_2$-2'), 1.69 (3H, s, H$_3$-8), 1.63 (3H, s, CH$_3$-7), 1.57 (3H, s, H$_3$-1'), 1.47 (3H, s, CH$_3$-3), 0.89 (3H, t, J=7.5 Hz, H$_3$-3')
$^{13}$C-NMR: δ=131.7, 124.1, 104.0, 87.3, 72.5, 69.8, 48.3, 44.8, 31.6, 29.1, 25.7, 23.4, 23.1, 17.6, 8.9.

EXAMPLE 3

Phosphoric Acid Catalyzed IPM-Addition to Ethynyl-β-Ionol

Reaction

A mixture of 54.8 g of ethynyl-β-ionol (0.245 Mol) and 69.7 g of IPM (0.932 Mol) was stirred (magnetic stirrer) in a 250 ml 3-neck round bottomed flask under argon at a $T_f=-20°$ C. ($T_f=$ca. $-25°$ C.). 0.132 g of catalyst solution (H$_3$PO$_4$, 18.1 w % in acetone, 0.245 mMol=0.1 Mol % relative to ethynyl-β-ionol) were added at once with the help of a volume adjustable pipette with disposable tip. The clear and colorless solution was stored for 72 hours at $T_f=-28°$ C. in a deep freezer of ca. $-22°$ C. Out of the deep-freezer, still at $T_f=-20°$ C., under stirring and argon, the solution was set basic with 103 µl triethylamine and stirred until room temperature was reached. The reaction mixture was then concentrated on a rota-vapor with a membrane-pump (10 mbar) and degassed with a high-vacuum pump (0.02 mbar on pump). During this process and the following work-up the temperature of the ethynyl-β-ionol-IPM-adduct should not exceed 22-25° C. 73 g of the crude product were isolated, containing 95.7 area % ethynyl-β-ionol-IPM-adduct, yield 98.3%.

Purification was achieved by the method described above. 71.3 g of product, purity 97.0%, yield 97.4%, was obtained.

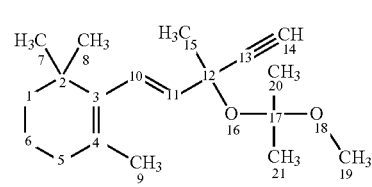

Formula

Molecular formula $C_{19}H_{30}O_2$
Monoisotopic mass 290.45
Chemical name (CAS) 2-[(E)-3-(1-Methoxy-1-methylethoxy)-3-methyl-pent-1-en-4-ynyl]-1,3,3-trimethyl-cyclohexene
$^1$H-NMR (CDCl$_3$) δ in ppm: 0.94 (6H, s, H-7+H-8), 1.40-1.36 (2H, m, H1+H6), 1.39 (3H, s, H-20 or H-21), 1.45 (3H, s, H-20 or 21), 1.50-1.56 (2H, m, H1+H6), 1.53 (3H, s, H-15), 1.61 (3H, d, $^4$J=0.80 Hz, H-9), 1.91 (2H, br t, $^3$J=6.03 Hz, H-5), 2.56 (1H, s, H-14), 3.19 (3H, s, H-19), 5.46 (1H, d, $^3$J=16.02 Hz, H11), 6.35 (1H, dd, $^5$J=0.80 Hz; $^3$J=16.02 Hz, H-10).
$^{13}$C-NMR (CDCl$_3$) δ in ppm: 136.0 (C-11), 135.5 (C-3), 127.7 (C-4), 126.3 (C-10), 101.1 (C-17), 84.6 (C-13), 73.5, (C-14), 70.0 (C-12), 47.3 (C-19), 38.5 (C-1 or C-6), 33.4 (C-2), 32.0 (C-15), 31.7 (C-5), 27.6-27.7 (C-7+C-8), 25.2-25.7 (C-20+C-21), 20.1 (C-9), 18.3 (C-1 or C-6).

EXAMPLE 4

Phosphoric Acid Catalyzed IPM-Addition to Vinyl-β-Ionol

Reaction

A mixture of 18.4 g of vinyl-β-ionol (0.081 Mol) and 23.1 g of IPM (0.309 Mol) was stirred (magnetic stirrer) in a 250 ml 3-neck round bottomed flask under argon at a $T_f=-20°$ C. ($T_f=$ca. $-25°$ C.). 0.0438 g of catalyst solution (H$_3$PO$_4$ 18.1 w % in acetone, 0.081 mMol=0.1 Mol % relative to vinyl-β-ionol) were added at once with the help of a volume adjustable pipette with disposable tip. This clear and colorless solution was stored for 72 hours in a freezer at $T_f=0°$ C. Out of the deep-freeze the solution was set basic with 34 µl of triethylamine and stirred until room temperature was reached. The reaction mixture was then concentrated on a rota-vapor with a membrane-pump (10 mbar) and degassed with a high-vacuum pump (0.02 mbar on pump). During this process and the following work-up the temperature of the vinyl-β-ionol- IPM-adduct should not exceed 22-25° C. 22.8 g of crude product were isolated, containing 65 area % vinyl-β-ionol-IPM-adduct, yield 62.3%. Final purification was achieved in accordance with the method described above. The product could be isolated in 54.7% yield (15 g, 87% purity).

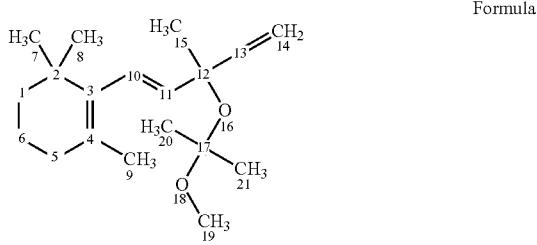

Formula

Molecular formula $C_{19}H_{32}O_2$
Monoisotopic mass 292.44
Chemical name (CAS) 2-[(E)-3-(1-Methoxy-1-methyl-ethoxy)-3-methyl-penta-1,4-dienyl]-1,3,3-trimethyl-cyclohexene $^1$H-NMR (CDCl$_3$) δ in ppm: 0.92 (6H, s, H-7+H-8), 1.39-1.37 (2H, m, H-1+H-6), 1.35 (3H, s, H-20 or H-21), 1.36 (3H, s, H-20 or H-21), 1.44 (3H, s, H-15), 1.57-1.49 (2H, m, H-1+H-6), 1.60 (3H, d, $^4$J=0.75 Hz, H-9), 1.90 (2H, br t, $^3$J=5.88 Hz, H-5), 3.17 (3H, s, H-19), 4.97 (1H, dd, $^3$J=10.74 Hz; $^5$J=1.40 Hz, H-14$_Z$), 5.13 (1H, dd, $^3$J=17.65 Hz; $^5$J=1.40 Hz, H-14$_E$), 5.53 (1H, d, $^3$J=16.30 Hz, H-11), 5.93 (1H, dd, $^3$J=16.30 Hz; $^5$J=0.94 Hz, H-10), 6.03 (1H, dd, $^3$J=10.74 Hz; $^3$J=17.65 Hz, H-13).

$^{13}$C-NMR (CDCl$_3$) δ in ppm: 143.4 (C-13), 138.5 (C-11), 136.1 (C-3), 127.2 (C-4), 124.6 (C-10), 110.9 (C-14), 100.3 (C-12), 76.8 (C-17), 47.2 (C-19), 38.5 (C-1 or C-6), 33.3 (C-2), 31.7 (C-5), 27.8 (C-7+C-8), 26.3-25.2 (C-20+C-21), 20.3 (C-9), 18.3 (C-1 or C-6).

NMR Parameter:
NMR spectra were recorded on a Bruker Avance 300 spectrometer equipped with 5 mm BBO BB-1H probe head operating at 300 MHz for $^1$H and 75.5 MHz for $^{13}$C. Spectra were recorded in CDCl$_3$ and referenced to TMS (δ$_H$) or solvent signals (δ$_C$): δ$_H$0.00/δ$_C$ 77.0. Assignments were based on $^1$H and $^{13}$C-NMR spectral data taking into account coupling constants and chemical shifts.

EXAMPLE 5

Thermal Cleavage of MBE-IPM-Adduct Followed by Phosphoric Acid Catalyzed Synthesis to MH with Additional IPM A 33 ml stainless steel autoclave was charged with 5 g of MBE-IPM-adduct, 96.4 area % (30.5 mMol) and shacked at 250 min$^{-1}$ in a "Lab Shaker" with a heating block of T$_j$ 150° C. for 16 hours. The autoclave was entirely cooled down to room temperature and the net weight was measured. After a sampling for GC w % was done, 25.2 mg of catalyst solution (H$_3$PO$_4$, 17.7 w % in acetone, 0.046 mMol=0.15 Mol % relative to MBE-IPM-adduct) were added at once with the help of a volume adjustable pipette with disposable tip. Then 5.71 g of IPM, 96.5 area % (76.4 mMol), were added. The closed autoclave was placed for another 16 hours at the same conditions as described above in the "Lab Shaker". The autoclave was entirely cooled down to room temperature and the net weight was measured. The autoclave was opened and the reaction mixture neutralized under magnetic stirring with 20 µl of triethylamine. A sampling was done for GC area % and weight %. Yield: 86%.

EXAMPLE 6

Thermal Cleavage of MBE-IPM-Adduct Followed by Phosphoric Acid Catalyzed Synthesis to MH without Additional IPM When the same procedure was carried out as described in Example 5, however, without addition of IPM, MH was obtained in a yield of 60%.

EXAMPLE 7

MBE-IPM-adduct+DMP in Presence of Acid to Form MH

To a 33 ml stainless steel autoclave 5 g of MBE-IPM-adduct (30.7 mMol) and 8.34 g of DMP, 96% (76.9 mMol, 2.5 equiv.) were charged. Under stirring 24.9 mg of the catalyst solution (H$_3$PO$_4$, 18.15 weight % in acetone, 0.046 mMol=0.15 Mol % relative to adduct) were added at once via an adjustable pipette with disposable tip. the closed autoclave was placed in a "Lab Shaker" with a heating block of T$_j$ 150° C. and shaken at 250 min$^{-1}$ for 8, 16, 24 and 32 hours, respectively. The autoclave was first cooled with water and then to room temperature over 3 hours. The autoclave was opened and the reaction mixture neutralized under stirring with 19.4 µl of triethylamine. The net weights of MH were measured and samplings were done for GC area % and weight %. The yields were 47.1%, 70.0%, 78.3% and 78.8%, respectively.

EXAMPLE 8

Phosphoric Acid Catalyzed Reaction of MBE with DMP to Form MH

A 33 ml stainless steel autoclave equipped with a magnetic stirrer was charged with 3.19 g of MBE, (36.2 mMol) and 9.81 g of DMP, 96% (90.4 mMol, 2.5 equiv.). Under stirring 29.3 mg of catalyst solution (H$_3$PO$_4$ 18.15% in acetone, 0.054 mMol=0.15 Mol % relative to MBE) were added at once via a volume adjustable pipette with disposable tip. The closed autoclave was placed in a "Lab Shaker" with a heating block of T$_j$ 150° C. and shaken at 250 min$^{-1}$ for 8, 16, 24 and 32 hours, respectively. The autoclave was first cooled with water and then to room temperature over 3 hours. The autoclave was opened and the reaction mixture neutralized under stirring with 22.8 µl of triethylamine. The net weights were measured and samplings were done for GC area % and weight %. The yields of MH after 8, 16, 24 and 32 hours were 38.6%, 46.0%, 51.2% and 52.0%, respectively.

The invention claimed is:
1. Allyl and propargyl ethers of the general formula (I):

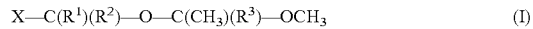

$$X—C(R^1)(R^2)—O—C(CH_3)(R^3)—OCH_3 \quad (I)$$

wherein,
X is an ethynyl or vinyl group,
R$^1$ is methyl or ethyl,
R$^2$ is methyl, CH$_2$-prenyl, CH$_2$-geranyl, CH$_2$-farnesyl, CH$_2$-hexa-hydrofarnesyl, CH$_2$-solanesyl or CH═CH-(2.6.6-trimethylcyclohex-1-enyl), and
R$^3$ is methyl or ethyl.

2. The compound of claim 1 which is 3-(1-methoxy-1-methylethoxy)-3-methyl-1-butene.

3. A compound of claim 1, in a purity of at least 80%.

4. A compound of claim 1, in a purity of at least 95%.

5. A process for the preparation of a compound as claimed in claim 1, wherein the process comprises reacting a tertiary ethynyl or vinyl carbinol of formula (II):

$$X-C(R^1)(R^2)-OH \qquad (II),$$

wherein X, $R^1$ and $R^2$ are as defined previously, with isopropenyl methyl ether (IPM) or 2-n-butenyl methyl ether (BME) at a temperature of −20° C. or below, in the presence of an acid as catalyst.

6. The process of claim 5 wherein the acidic catalyst is phosphoric acid.

7. The process of claim 5, which further comprises after termination of the reaction, the step of neutralizing the reaction mixture with a weak base.

8. The process of claim 7, wherein the base is triethylamine.

9. A method of manufacturing β-ketoallenes, α,β-unsaturated carbonyl compounds or γ,δ-unsaturated ketones by using a compound of claim 1 as an intermediate.

10. A method of manufacturing 6-methyl-5-hepten-2-one by using 3-(1 methoxy-1-methylethoxy)-3-methyl-1-butene as an intermediate.

11. A method for the manufacture of a β-ketoallene or a γ,δ-unsaturated ketone which comprises heating a compound of formula (I) as defined in claim 1 to 100-160° C., optionally in the presence of a catalyst, and optionally with additional isopropenyl methyl ether (IPM).

12. The method of claim 11, which comprises forming 6-methyl-5-heptene-2-one from 3-(1-methoxy-1-methylethoxy)-3-methyl-1-butene.

13. A method for the manufacture of a β-ketoallene or an unsaturated ketone according to claim 11, wherein the compound of formula (I) is an adduct of linalool, dehydrolinalool, nerolidol, 2-solanesyl-1-methyl-1-ethinyl-ethanol, vinyl-β-ionol or ethynyl-β-ionol with IPM isopropenyl methyl ether (IPM) or 2-n-butenyl methyl ether (BME).

14. A method as in claim 11, wherein the compound of formula (I) is heated to 120-150° C.

15. A method as in claim 11, wherein the compound of formula (I) is heated in the presence of an acid.

16. A method for the preparation of a γ,δ-unsaturated ketone of formula (IV):

$$(R1)(R2)C=Y-CH_2-CO-R3 \qquad (IV),$$

wherein R1 methyl or ethyl; R2 is a saturated or unsaturated linear or cyclic aliphatic hydrocarbon residue, R3 is methyl or ethyl; and Y is C=CH or CH—CH2, wherein the method comprises reacting a compound of formula (I) as claimed in claim 1 with 2,2-dimethoxypropane (DMP) in the presence of an acid.

17. The method of claim 16, wherein the compound of formula (I) is 3-(1-methoxy-1-methylethoxy)-3-methyl-1-butene, and the compound of formula (IV) is 6-methyl-5-hepten-2-one (MH).

18. The method of claim 16, wherein the acid is phosphoric acid.

19. A method for the preparation of 6-methyl-5-hepten-2-one (MH) which comprises reacting 2-methyl-3-buten-2-ol (MBE) with 2,2-dimethoxypropane (DMP) in the presence of phosphoric acid as catalyst.

20. 3-(1-methoxy-1-methylethoxy)-3-methyl-5-(2,6,6-trimethyl-cyclohex-1-enyl)-1-pentyne-4-ene.

21. 3-(1-methoxy-1-methylethoxy)-3-methyl-5-(2,6,6-trimethyl-cyclohex-1-enyl)-1,4-pentadiene.

* * * * *